US012383614B2

(12) United States Patent
Chen et al.

(10) Patent No.: US 12,383,614 B2
(45) Date of Patent: Aug. 12, 2025

(54) MUTANTS OF RESPIRATORY SYNCYTIAL VIRUS FUSION PROTEINS

(71) Applicant: YIKANG BIOTECH (SUZHOU) CO., LTD., Jiangsu (CN)

(72) Inventors: Lei Chen, Suzhou (CN); Yujiao Song, Suzhou (CN); Min Dai, Suzhou (CN); Xin Xie, Suzhou (CN); Shibi Zhao, Suzhou (CN); Jiahao Xu, Suzhou (CN); Yujuan Hua, Suzhou (CN); Chao Wu, Suzhou (CN); Sufang Gu, Suzhou (CN); Tao Fang, Suzhou (CN); Li Chen, Suzhou (CN); Jiadi Huang, Suzhou (CN); Xiaoya Ding, Suzhou (CN); Mingze Shi, Suzhou (CN); Peizhe Li, Suzhou (CN); Jiaxin Lei, Suzhou (CN); Guangsha Zhang, Suzhou (CN); Meng Zhang, Suzhou (CN); Wendie Wang, Suzhou (CN); Ruihong Jiang, Suzhou (CN); Songming He, Suzhou (CN); Derong Wang, Suzhou (CN); Tengsen Gao, Suzhou (CN); Eric Chen, Suzhou (CN); Jianguo Yin, Suzhou (CN)

(73) Assignee: YIKANG BIOTECH (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 19/017,356

(22) Filed: Jan. 10, 2025

(65) Prior Publication Data
US 2025/0205329 A1   Jun. 26, 2025

Related U.S. Application Data

(63) Continuation-in-part of application No. PCT/CN2024/087839, filed on Apr. 15, 2024.

(30) Foreign Application Priority Data

Dec. 21, 2023 (CN) .......................... 202311774986.3

(51) Int. Cl.
| | | |
|---|---|---|
| A61K 39/155 | (2006.01) | |
| A61K 39/00 | (2006.01) | |
| A61P 31/14 | (2006.01) | |
| C07K 14/005 | (2006.01) | |
| C12N 7/00 | (2006.01) | |

(52) U.S. Cl.
CPC ............ *A61K 39/155* (2013.01); *A61P 31/14* (2018.01); *C07K 14/005* (2013.01); *C12N 7/00* (2013.01); *A61K 2039/575* (2013.01); *C07K 2319/50* (2013.01); *C12N 2760/18522* (2013.01); *C12N 2760/18534* (2013.01)

(58) Field of Classification Search
CPC . A61K 39/155; A61K 2039/575; A61P 31/14; C07K 14/005; C07K 2319/50; C12N 7/00; C12N 2760/18522; C12N 2760/18534
See application file for complete search history.

(56) References Cited

U.S. PATENT DOCUMENTS

| | | | |
|---|---|---|---|
| 9,738,689 B2* | 8/2017 | Kwong | ................ C07K 14/005 |
| 2018/0177864 A1 | 6/2018 | Che et al. | |
| 2019/0330277 A1 | 10/2019 | Chen et al. | |
| 2022/0017574 A1 | 1/2022 | Langedijk | |

FOREIGN PATENT DOCUMENTS

| | | |
|---|---|---|
| CN | 110054668 A | 7/2019 |
| CN | 116003536 A | 4/2023 |
| CN | 116284266 A | 6/2023 |
| CN | 117106036 A | 11/2023 |
| WO | 2008147196 A2 | 12/2008 |
| WO | 2014140083 A1 | 9/2014 |

OTHER PUBLICATIONS

McLellan et al (2013). Structure-based design of a fusion glycoprotein vaccine for respiratory syncytial virus. Science. Nov. 1, 2013;342(6158):592-8. (Year: 2013).*
Stewart-Jones et al (2015). A Cysteine Zipper Stabilizes a Pre-Fusion F Glycoprotein Vaccine for Respiratory Syncytial Virus. PLoS One. Jun. 22, 2015;10(6):e0128779. (Year: 2015).*
Krarup et al (2015). A highly stable prefusion RSV F vaccine derived from structural analysis of the fusion mechanism. Nat Commun. Sep. 3, 2015;6:8143. (Year: 2015).*
Swanson et al (2014). A monomeric uncleaved respiratory syncytial virus F antigen retains prefusion-specific neutralizing epitopes. J Virol. Oct. 2014;88(20):11802-10 (Year: 2014).*

(Continued)

*Primary Examiner* — Janet L Andres
*Assistant Examiner* — Samadhan Jaising Jadhao
(74) *Attorney, Agent, or Firm* — Poseidon Advanced IP LLC

(57) ABSTRACT

The present disclosure relates to the field of biomedicine, and in particular, to an improved mutant of a respiratory syncytial virus (RSV) fusion (F) protein and uses thereof. The mutant can form a trimeric structure without introducing a heterologous trimerization domain. Meanwhile, through mutation designs such as releasing internal electrostatic repulsion, deleting the furin cleavage site, truncating the C-terminal domain, and introducing interchain disulfide bonds, the protein is stabilized in the pre-fusion conformation and exhibits enhanced stability. The mutant in the present disclosure is highly immunogenic when used as a vaccine or a vaccine component and can induce the production of a high level of neutralizing antibodies in the immunized animal, which can be used in the preparation of a vaccine for the prevention or treatment of RSV infection, and can also be used as a reagent for the detection of RSV.

10 Claims, 6 Drawing Sheets
Specification includes a Sequence Listing.

(56) References Cited

OTHER PUBLICATIONS

Zimmer et al (2002). Cleavage at the furin consensus sequence RAR/KR(109) and presence of the intervening peptide of the respiratory syncytial virus fusion protein are dispensable for virus replication in cell culture. J Virol. Sep. 2002;76(18):9218-24. (Year: 2002).*

Liang et al (2017). Improved Prefusion Stability, Optimized Codon Usage, and Augmented Virion Packaging Enhance the Immunogenicity of Respiratory Syncytial Virus Fusion Protein in a Vectored-Vaccine Candidate. J Virol. Jul. 12, 2017;91(15):e00189-17. (Year: 2017).*

The Second Office Action in Chinese Application No. 202311774986.3 mailed on Sep. 6, 2024, 11 pages.

Notification to Grant Patent Right for Invention in Chinese Application No. 202311774986.3 mailed on Oct. 18, 2024, 5 pages.

Krarup, A. et al., A Highly Stable Prefusion RSV F Vaccine Derived from Structural Analysis of the Fusion Mechanism, Nature Communications, 2015, 12 pages.

Blais, N. et al., Characterization of Pre-F-GCN4t, a Modified Human Respiratory Syncytial Virus Fusion Protein Stabilized in a Noncleaved Prefusion Conformation, Journal of Virology, 2017, 18 pages.

Sun, Yuchen et al., Advance in development of PreF-Based Vaccines Against Respiratory Syncytial Virus, Progress in Microbiology and Immunology, 50(6): 58-64, 2022.

Griffin, M. R., A Challenge to Respiratory Syncytial Virus Illness in Adults, New England Journal of Medicine, 386(25): 2427-2428, 2022.

McLellan, J. S. et al., Structure-Based Design of a Fusion Glycoprotein Vaccine for Respiratory Syncytial Virus, Science, 2013, 8 pages.

Harshbarger, W. et al., Improved Epitope Resolution of the Prefusion Trimer-Specific Antibody AM14 Bound to the RSV F Glycoprotein, MABS, 2021, 13 pages.

* cited by examiner

SEQ ID NO. 4

MKWVTFLLLLFISGSAFSQNITEEFYQSTCSAVSKGYLSALRTGWYTSVITIELSNIKENKCN
GTDAKVKLIKQELDKYKNAVTELQLLMQSTPAANS|......|GVGSAIASGIAVSKVLHLEGEV
NKIKSALLSTNKAVVSLSNGVSVLTSKVLDLKNYIDKQLLPIVNKQSCSISNIETVIEFQQKN
NRLLEITREFSVNAGVTTPVSTYMLTNSELLSLINDMPITNDQKKLMSSNVQIVRQQSYSIM
SIIKEEVLAYVVQLPLYGVIDTPCWKLHTSPLCTTNTKEGSNICLTRTDRGWYCDNAGSVSF
FPQAETCKVQSNRVFCDTMNSLTLPSEVNLCNIDIFNPKYDCKIMTSKTDVSSSVITSLGAIV
SCYGKTKCTASNKNRGIIKTFSNGCDYVSNKGVDTVSVGNTLYYVNKQEGKSLYVKGEPII
NFYDPLVFPSDEFDASISQVNEKINQSLAFIRKSSKVLHLEGEVNKIKSALLS

MUTANTS OF RESPIRATORY SYNCYTIAL VIRUS FUSION PROTEINS

CROSS-REFERENCE TO RELATED APPLICATION

This application is a continuation-in-part of International Application No. PCT/CN2024/087839, filed on Apr. 15, 2024, which claims priority to the Chinese Patent Application No. 202311774986.3, filed on Dec. 21, 2023, the contents of each of which are hereby incorporated by reference in its entirety.

SEQUENCE LISTING

The instant application contains a Sequence Listing which has been submitted electronically in XML format and is hereby incorporated by reference in its entirety. The XML copy, created on Dec. 30, 2024, is named "2024 Dec. 30-Sequence Listing-20957-0001US00" and is 6,825 bytes in size.

TECHNICAL FIELD

The present disclosure relates to the field of biomedical technology, and in particular, to improved mutants of respiratory syncytial virus (RSV) fusion (F) proteins and uses thereof.

BACKGROUND

Respiratory syncytial virus (RSV) is a common respiratory virus; infected cells will fuse to form a large cellular structure similar to the "syncytium." The clinical manifestation of infection is upper respiratory tract disease, which can further develop into lower respiratory tract disease. It is an important viral pathogen that causes acute lower respiratory illness (ALRI) in infants, young children, the elderly, and immunocompromised adults. In young children, respiratory syncytial virus infections manifest with capillary bronchiolitis, pneumonia, and tracheobronchitis. The elderly and immunocompromised adults experience more severe manifestations, including capillary bronchiolitis, pneumonia, asthma, chronic obstructive pulmonary disease exacerbation, congestive heart failure exacerbation, etc.

RSV infection is mainly mediated by the transmembrane envelope glycoproteins, fusion (F) protein, and attachment (G) protein. Although both F and G proteins are located outside the viral envelope and have multiple specific antigenic determinants, the sequences of the F proteins are highly conserved among the different isoforms. Vaccines using F proteins as antigens are expected to stimulate the body to produce a broader spectrum of protection, which makes F proteins an important candidate antigen for RSV vaccines. During the fusion of the viral envelope with the host cell membrane, the F protein shifts from a sub-stable pre-fusion conformation to a stable post-fusion conformation. A large amount of preclinical and clinical data suggests that a vaccine having the RSV F protein in the pre-fusion conformation as the antigen can stimulate the body to produce higher levels of virus-neutralizing antibodies (Griffin, M. R. (2022). "A Challenge to Respiratory Syncytial Virus Illness in Adults." N Engl J Med 386 (25): 2427-2428). However, the RSV F protein in the pre-fusion conformation is susceptible to conversion to the post-fusion conformation after physical or chemical stress or storage (McLellan, J. S., et al. (2013). "Structure-based design of a fusion glycoprotein vaccine for respiratory syncytial virus." Science 342 (6158): 592-598). Thus, F proteins need to be engineered to maintain the stability of the pre-fusion conformation.

Currently, two prophylactic RSV vaccines, Arexvy and Abrysvo, which are based on the fusion of the pre-fusion conformation F protein as an antigen, have been approved for marketing. However, no relevant prophylactic vaccine products have been approved for marketing in China. Arexvy, developed by GSK, consists of the F protein in the pre-fusion conformation combined with adjuvant system 01 (AS01E), and Abrysvo, developed by Pfizer, consists of a bivalent F protein in the pre-fusion conformation as the antigen. The former vaccine is used in the U.S. for people aged 60 years and older, and the latter vaccine is used in pregnant women and people aged 60 years and older. However, both Arexvy and Abrysvo suffered from suboptimal durable protection after immunization, with reported immunoprotection rates of 66.7% (LRTD2+) and 82.6% (LRTD) in the first epidemic season, which declined to 48.9% (LRTD2+) and 56.1% (LRTD) in the second epidemic season, and booster vaccination in the second epidemic season failed to boost the immunoprotection rate.

The antigens of both Arexvy and Abrysvo vaccines were designed to replace the C-terminal transmembrane insoluble region with foldon, a heterologous trimerization domain, in order to allow soluble expression of the proteins and to maintain a trimerized conformation. However, the use of the heterologous trimerization domain tends to produce pre-existing immunity, which makes it difficult to provide sustained protection through repeated vaccination when vaccine immunity durability is not optimal. Therefore, it is desired to provide an improved RSV F protein in the pre-fusion conformation without introducing the heterologous trimerization domain to provide sustained immune protection.

SUMMARY

In order to solve the above problems, the present disclosure provides an improved mutant of a respiratory syncytial virus (RSV) fusion (F) protein, which can stably present a trimerized conformation without introducing a heterologous trimerization domain, ensuring that the protein is similar to its natural conformation, and provides a new direction for clinical application and lays the foundation for the development of new products to prevent and block RSV infection.

The present disclosure focuses on research on the RSV F protein, designing a specific mutant that can stably present a pre-fusion conformation based on the guidance of structural biology and bioinformatics. The mutant of the RSV F protein can, in comparison to the wild-type F protein, form a trimeric structure without introducing the heterologous trimerization domain. The designed mutations make the mutant in a more stable pre-fusion state, enabling large-scale soluble expression of the target protein in mammalian cells, with excellent protein stability. The mutant, when used as a vaccine or a component of a vaccine, exhibits enhanced immunogenicity and can induce higher levels of neutralizing antibodies in immunized animals. The mutant of the RSV F protein described in the present disclosure may be used for the prevention and/or treatment of RSV infections and may also be used as a reagent for the detection of RSV. The mutant for the prevention and/or treatment of RSV infections may be used alone, in combination with different adjuvants to form vaccine compositions, or in conjunction with different types of vaccine products to form multivalent vaccines.

One embodiment of the present disclosure provides an improved mutant of an RSV F protein. The improved mutant may be obtained by replacing a C-terminal transmembrane insoluble region of the RSV fusion F protein with a segment of a soluble region of the RSV F protein.

In some embodiments, the segment of the soluble region of the RSV F protein may be a rigid structure.

In the present disclosure, a segment with a rigid structure from a soluble expression region of the RSV F protein is used to replace its C-terminal transmembrane insoluble region. This not only enables the soluble expression of the target protein but also allows it to form a trimeric conformation without the introduction of any exogenous trimerization domain. This ensures that the protein maintains a conformation similar to the natural state, which can help avoid pre-existing immunity when used as a component of a vaccine.

In some embodiments, the RSV F protein may have an amino acid sequence of SEQ ID NOs. 1-3. The segment of the soluble region of the RSV F protein may have an amino acid sequence from positions 155 to 173, from positions 190 to 204, or from positions 255 to 275 of SEQ ID NOs. 1-3.

In some embodiments, the C-terminal transmembrane insoluble region of the RSV F protein may have an amino acid sequence from position 510 to the last position of SEQ ID NOs. 1-3.

In some embodiments, the improved mutant may be obtained by mutating lysine at position 508 and serine at position 509 (K508C and S509C) of SEQ ID NOs. 1-3 to cysteine, respectively.

In the present disclosure, the rigid structure of the segment of the soluble region is a non-trimeric conformation in its natural state. To further increase the interaction force of trimers, the K508C-S509C mutations immediately adjacent to the C-terminal are introduced. The introduction of interchain disulfide bonds can increase the interaction between the C-terminal of the trimer and is classified as a C-terminal mutation.

In some embodiments, the improved mutant may further include at least one disulfide bond mutation.

In the present disclosure, since the wild-type RSV F protein does not have any interchain disulfide bonds between the trimers, the mutation of the interchain disulfide bonds may further enhance the stability of the trimers.

In some embodiments, the improved mutant may include at least one of the mutations, including respectively mutating alanine at position 74 and glutamic acid at position 218 of SEQ ID NOs. 1-3 to cysteine (A74C, E218C) and respectively mutating glutamine at position 279 and alanine at position 241 of SEQ ID NOs. 1-3 to cysteine (Q279C, A241C).

In some embodiments, the improved mutant may further include mutating each of one or more charged amino acids in the amino acid sequence of the RSV F protein to a polar amino acid, a hydrophobic amino acid, or an aromatic amino acid to release electrostatic repulsion in the RSV F protein and enhance the stability of the RSV pre-fusion protein.

In some embodiments, the improved mutant may include at least one of the mutations, including mutating glutamic acid at position 60 of SEQ ID NOs. 1-3 to alanine (E60A), glycine (E60G), serine (E60S), threonine (E60T), leucine (E60L), methionine (E60M), or phenylalanine (E60F).

In some embodiments, the improved mutant may further include removing a segment containing a furin cleavage site of the amino acid sequence of the RSV F protein.

In the present disclosure, removing the segment containing the furin cleavage site avoids the breakage caused by furin cleavage in the wild-type RSV F protein, which in turn maintains the pre-fusion conformation. In the present disclosure, site-directed mutations without the introduction of any furin protease cleavage sites are employed, and there is no need to introduce heterologous linker sequences. This approach maintains a higher sequence similarity compared to the wild-type sequence.

In some embodiments, the improved mutant may be obtained by removing 28 to 46 amino acids from positions 100 to 147 of SEQ ID NOs. 1-3.

In some embodiments, the improved mutant may be obtained by removing 37 amino acids between positions 105 and 143 of SEQ ID NOs. 1-3 (deletion of 37 amino acids between positions 105 and 143).

One embodiment of the present disclosure provides a nucleic acid molecule for encoding the improved mutant of the RSV F protein.

In some embodiments, the nucleic acid molecule is codon-optimized for expression in mammalian cells.

One embodiment of the present disclosure provides a vector including the nucleic acid molecule.

One embodiment of the present disclosure provides a cell, the cell expressing the improved mutant of the RSV F protein, or including the nucleic acid molecule or the vector.

One embodiment of the present disclosure provides a vaccine including the improved mutant of the RSV F protein.

In some embodiments, the vaccine may include other active ingredients.

In some embodiments, the vaccine may further include a vaccine adjuvant.

One embodiment of the present disclosure provides a pharmaceutical composition including the improved mutant of the RSV F protein, the vaccine, the nucleic acid molecule, or the vector.

In some embodiments, the pharmaceutical composition includes one or more pharmaceutically acceptable excipients.

In some embodiments, the pharmaceutically acceptable excipients include a protectant, a stabilizer, a preservative, a bactericide, an inactivator, an adjuvant, and/or a buffering agent.

One embodiment of the present disclosure provides the use of the improved mutant of the RSV F protein, the nucleic acid molecule, the vector, the cell, the vaccine, or the pharmaceutical composition in the preparation of a product that detects, prevents, or treats RSV infection.

Further, the use may include the following steps:
When the product is prepared for detecting RSV infection, using the mutant of the RSV F protein described above or produced by the nucleic acid molecule, the vector, or the cell as a coating reagent for a detection kit and determining whether a sample is suffering from RSV infection by detecting the titer of a binding antibody in the sample; and
When the product is prepared for preventing or treating RSV infection, administering, by an immune route, the mutant of the RSV F protein described above or produced by the nucleic acid molecule, the vector, or the cell alone or in combination with an adjuvant, the vaccine, or the pharmaceutical composition to stimulate the body to produce a neutralizing antibody for the prevention or treatment of RSV infection.

By means of the above embodiments, the present disclosure has at least the following advantages:

The present disclosure provides the design of an improved mutant of the RSV F protein. At the C-terminal end of the improved mutant of the RSV F protein, the insoluble transmembrane region is replaced with a segment of the soluble region of the RSV F protein, which enables large-scale soluble expression of the target protein using mammalian cells and allows the formation of a trimeric structure without using the heterologous trimerization domain. This avoids the pre-existing immunity defect of the F protein caused by the introduction of a heterologous trimerization domain in existing technologies.

In addition, the designed mutations keep the RSV F protein in a more stable pre-fusion state, and the protein stability is excellent. The mutant of the RSV F protein has enhanced immunogenicity when used as a vaccine or a vaccine component and is capable of inducing higher levels of neutralizing antibodies in immunized animals. The mutant of the RSV F protein can be used in the preparation of a recombinant protein RSV vaccine for the prevention and/or treatment of diseases and conditions caused or mediated by RSV.

The above description is only an overview of the technical program and some of the results of the present disclosure. In order to more clearly understand the technical means of the present disclosure and implement it in accordance with the contents of the present disclosure, better embodiments of the present disclosure and the detailed accompanying drawings are described below.

BRIEF DESCRIPTION OF THE DRAWINGS

FIG. 1 is a diagram illustrating a template amino acid sequence (SEQ ID NO. 4) for constructing a mutant of an RSV F protein according to some embodiments of the present disclosure, where the template amino acid sequence includes a heterologous signal peptide sequence shown by the underline, F2 polypeptide (residues 26-109), "| . . . |" denotes deletion of 37 amino acids between position 105 and position 143, F1 polypeptide (residues 143-509), and substitution sequences (shown in bold black font, residues 155-173); the positions of the amino acids are relative to corresponding positions of an amino acid sequence of a wild-type RSV F protein as set forth in any one of SEQ ID NOs. 1-3;

FIG. 5 is a schematic diagram illustrating a size exclusion chromatography (SEC) analysis of purified F proteins of the mutant YK001Ag399 and control molecules SC-TM, DS-CavI, and pXCS847.

DETAILED DESCRIPTION

Figure 2:
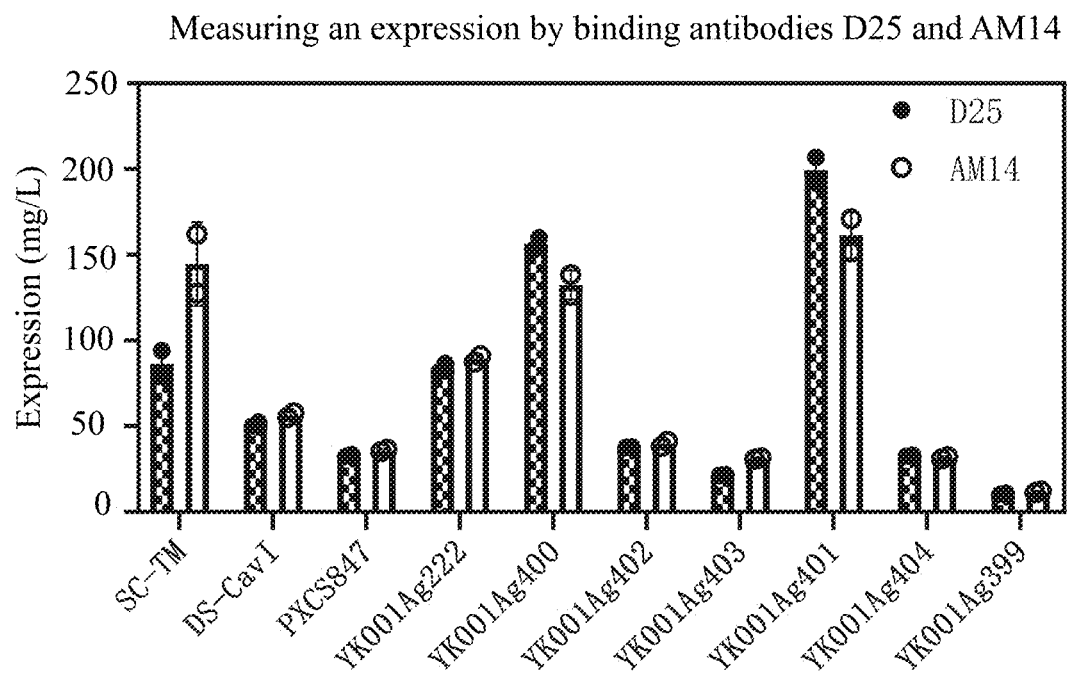
FIG. 2 is a graph illustrating measured F protein expression using pre-fusion F protein specific antibodies D25 and AM14, with SC-TM, DS-CavI, and pXCS847 as positive controls.

The present disclosure discloses an improved mutant of a respiratory syncytial virus (RSV) fusion F protein and uses thereof, which may be realized by a person skilled in the art by drawing on the contents herein and appropriately improving the process parameters. It is particularly noted that all similar substitutions and alterations will be apparent to one of skill in the art and that they are deemed to be encompassed by the present disclosure. The methods and uses of the present disclosure have been described by way of preferred embodiments. It is obvious that a person concerned can make alterations or appropriate changes and combinations to the methods and uses described herein without departing from the content, spirit, and scope of the present disclosure to realize and apply the technology of the present disclosure.

Terms are as follows.

In the present disclosure, the term "respiratory syncytial virus" or "RSV" belongs to the genus *Pneumovirus* of the family Paramyxoviridae. The viruses are often main viral pathogens that cause acute lower respiratory illness (ALRI) in infants, young children, the elderly, or immunocompromised adults, even causing interstitial pneumonia and bronchiolitis.

In the present disclosure, a protein mutant or a mutant of a protein generally refers to a protein that has one or more alterations in an amino acid sequence or protein structure thereof as compared to a wild-type protein. The alterations may include the deletion, insertion, substitution, truncation, and/or missing of one or more amino acids, and/or processing or cleavage of the protein structure. In the present disclosure, the protein mutant refers to the mutant of the RSV F protein.

In the present disclosure, an amino acid mutation generally refers to a modification of an amino acid in a parental amino acid sequence. For example, the modification may include a substitution, insertion, and/or missing of one or more amino acids. In the present disclosure, the amino acid mutation may include deletion or substitution of at least one amino acid residue at a specified position in an amino acid sequence. In some embodiments, the amino acid mutation may enable conformational optimization of a protein made up of the amino acids. The amino acid mutation may be generated using genetic or chemical methods. For example, genetic methods may include site-directed mutagenesis, polymerase chain reaction (PCR), gene synthesis, etc.

In the present disclosure, codon optimization generally refers to the replacement of one or more codons in a nucleic acid sequence encoding a parent peptide with codons that encode the same amino acids but have different usage frequencies. This is done to improve the expression of the nucleic acid encoding the polypeptide. In the present disclosure, as long as an amino acid is mutated in the same way as in the present disclosure, all possible codons encoding the mutated amino acid are covered by the present disclosure.

In the present disclosure, a trimer or a protein trimer generally refers to a protein structure consisting of three protein subunits of the same type or of different types, which may be linked together by a specific chemical structure. In the present disclosure, the protein trimer may be the RSV F protein.

In the present disclosure, a conformational change generally refers to a change in the spatial structure of a protein molecule. For example, the conformational change may include a change in the chemical bonding in the protein molecule, and modifications in the folding of the polypeptide.

In the present disclosure, a signaling peptide generally refers to an amino acid sequence present at the N-terminal of a transmembrane protein that serves as a signal for crossing the membrane. For example, the transmembrane protein may include secreted proteins or cell membrane proteins. For example, the signaling peptide may be synthesized at the N-terminal of the transmembrane protein as part of a precursor polypeptide.

In the present disclosure, a structural protein generally refers to a protein that includes components of virus particles. The structural protein may include structural proteins of the RSV. The structural protein of the present disclosure may include fusion (F) protein, attachment (G) protein, and small hydrophobic (SH) proteins of RSV.

In the present disclosure, the term "pre-fusion" or "pre-fusion" generally refers to the conformation of the structural protein before the virus infects the host cell and membrane fusion occurs. In general, a wild-type RSV F protein is a sub-stable state protein before fusion, and its conformation undergoes a discontinuous, gradual, and irreversible conformational change to a lower energy stable state conformation (post-fusion conformation) after the virus infects the host cell and accomplishes membrane fusion. In the present disclosure, a series of modifications are made to the RSV F protein such that the F protein mutant is stabilized in a pre-fusion state.

In the present disclosure, a protein mutation site is typically expressed by "amino acid+amino acid position+mutated amino acid". In the present disclosure, the mutation may include, but is not limited to, the addition, substitution, missing, and/or deletion of the amino acid. For example, the term "E218C" usually refers to the mutation of glutamic acid (E) to cysteine (C) at position 218.

In the present disclosure, the term "nucleic acid molecule" generally refers to an isolated form of nucleotide, deoxyribonucleotide, or ribonucleotide, of any length, or an analog isolated from its natural environment or synthesized.

In the present disclosure, a vector refers to a nucleic acid carrier into which a polyribonucleotide encoding a protein may be inserted to enable the expression of the protein. The vector may be transformed, transduced, or transfected into a host cell to enable the expression of elements of the genetic material it carries within the host cell. Merely by way of example, the vector includes plasmids, phages such as 2 phage or M13 phage and animal viruses, Coase plasmids, artificial chromosomes such as yeast artificial chromosomes (YAC), bacterial artificial chromosomes (BAC), or P1-derived artificial chromosomes (PAC). The animal viruses used as the vector include retroviruses (including lentiviruses), adenoviruses, adeno-associated viruses, herpesviruses (e.g., herpes simplex virus), poxviruses, baculoviruses, papillomaviruses, and human papillomaviruses (e.g., SV40). The vector may include a plurality of elements that control expression, including a promoter sequence, a transcription start sequence, an enhancer sequence, a selection element, and a reporter gene. Alternatively, the vector may also include a replication initiation site. The vector may also include components that assist in their entry into the cell or assist in the integration of a target element into the host cell, such as a viral particle, a liposome, a protein shell, or an integrase, etc. It should be noted that the vector may include other components which are not listed herein.

In the present disclosure, a pharmaceutical composition generally refers to a composition for the prevention or treatment of a disease or condition. The pharmaceutical composition may include a mutant of the RSV F protein, a nucleic acid molecule, a vector and/or a cell as described in the present disclosure, and an optionally pharmaceutically acceptable carrier. In addition, the pharmaceutical composition may include suitable formulation of one or more (pharmaceutically effective) adjuvants, stabilizers, excipients, diluents, solubilizers, surfactants, emulsifiers, and/or preservatives. The acceptable component of the composition is generally non-toxic to the recipient at the doses and concentrations used.

In the present disclosure, the pharmaceutically acceptable carrier generally includes pharmaceutically acceptable carrier agents, excipients, or stabilizers that are non-toxic to the cells or mammals to which they are exposed, at the doses and concentrations employed. The physiologically acceptable carrier may include buffers, antioxidants, low-molecular-weight (less than about 10 residues) peptides, proteins, hydrophilic polymers, amino acids, monosaccharides, disaccharides and other carbohydrates, chelating agents, sugar alcohols, salt-forming counter ions such as sodium, and/or nonionic surfactants, etc.

In the present disclosure, the term "include", "includes", or "including" and/or "comprise", "comprises", or "comprising" generally refer to including expressly designated features, but not excluding other elements.

The present disclosure is to design a novel protective vaccine based on structural biology, combined with the principles of immunology, with a high degree of safety, a broad protective power, and a reliable preparation process. The recombinant protein vaccine provided by the present disclosure is significantly more stable compared to the publicly reported DS-CavI and the preferred molecule 847 disclosed in the Pfizer's patent application. The mutant of the RSV F protein can be stabilized in the pre-fusion state and induce higher levels of neutralizing antibodies in immunization assays in animals when used alone or supplemented with a suitable adjuvant.

In the present disclosure, the adjuvant generally refers to any substance that aids or modulates the action of a drug, including, but not limited to, immunological adjuvants, which enhance or diversify the immune response to an antigen. In the present disclosure, the adjuvant may be used to enhance the antigenicity of the mutant of the RSV F protein. In some embodiments, the adjuvant may include a suspension of a mineral (e.g., alum, aluminum hydroxide, or phosphate). In some embodiments, the adjuvant may include an oil-in-water emulsion. In some embodiments, the adjuvant may include a liposome. In some embodiments, the adjuvant may include an immunostimulant such as MPL, CpG, Poly I: C, or the like.

In the present disclosure, the vaccine refers to a pharmaceutical composition including an immunogen capable of triggering a prophylactic or therapeutic immune response in an individual. Typically, a vaccine triggers an antigen-specific immune response against a pathogen, such as a viral pathogen.

In the present disclosure, a pre-fusion specific antibody refers to an antibody that specifically binds to an RSV F glycoprotein in the pre-fusion conformation but does not bind to an RSV F protein in the post-fusion conformation. An exemplary pre-fusion specific antibody includes antibodies D25, AM22, 5C4, MPE8, and AM14.

In the present disclosure, when an antibody binds to a given target molecule, the term "specifically binds" refers to a process of the antibody binding to a target molecule with a higher affinity than its binding to the other tested substance. For example, the affinity of an antibody that specifically binds to an RSV F protein in the pre-fusion conformation is higher than the affinity of the antibody that binds to an RSV F protein in the post-fusion conformation.

In the present disclosure, the term "SC-TM" refers to a RSV F protein having the amino acid sequence described in Krarup, A., et al. (2015). *A highly stable prefusion RSV F vaccine derived from structural analysis of the fusion mechanism*. Nat Commun 6:8143.

In the present disclosure, the term "847" refers to the pXCS847 molecule in patent application No. CN108738312A.

In the present disclosure, the term "DS-CavI" is the molecule described in Mclellan, J. S., et al. (2013). *Structure-based design of a fusion glycoprotein vaccine for respiratory syncytial virus*. Science 342 (6158): 592-598.

In the present disclosure, the term "D25" refers to an antibody described in patent application WO 2008/147196 A2 that specifically recognizes an RSV pre-fusion conformation of the F protein.

In the present disclosure, the term "AM14" refers to the antibody described in the literature by Wayne Harshbarger. et al. (2021) *Improved epitope resolution of the prefusion trimer-specific antibody AM14 bound to the RSV F glycoprotein*, mAbs, 13:1, DOI: 10.1080/19420862.2021.1955812, which only binds to a trimerized RSV F protein in the pre-fusion conformation and does not bind to the monomeric form of F protein.

In order not to be limited by any theory, the embodiments hereinafter set forth are intended solely to elucidate the mutant of the RSV F protein of the present disclosure, the preparation method, the quality characterization, the use, or the like, and are not intended to limit the scope of the present disclosure.

Mutant of RSV F Protein

The mutant of the RSV F protein may be obtained by altering a wild-type RSV F protein. RSV is an RNA virus, split into two major antigenic subgroups, A and B. The wild-type RSV F protein includes an F protein from the wild-type RSV A and/or the wild-type RSV B. In some embodiments, the F protein from the wild-type RSV A has an amino acid sequence of SEQ ID NO. 1. In some embodiments, the F protein from the wild-type RSV B has an amino acid sequence of SEQ ID NO. 2 or 3. In some embodiments, the wild-type RSV F protein has an amino acid sequence having at least 80%, 85%, 90%, 95%, 98% similarity with each of SEQ ID NOs. 1-3. In some cases, the wild-type RSV F protein may be referred to as the RSV F protein.

The altering the wild-type RSV F protein may include replacing a C-terminal transmembrane insoluble region of the RSV F protein with a segment of a soluble region of the RSV F protein, a disulfide bond mutation, a charged amino acid mutation, deletion of a segment containing a furin cleavage site, or the like, or any combination thereof. For example, the mutant of the RSV F protein may be obtained only by replacing a C-terminal transmembrane insoluble region of the RSV F protein with a segment of a soluble region of the RSV F protein, a disulfide bond mutation, a charged amino acid mutation, or deletion of a segment containing a furin cleavage site in comparison to the wild-type RSV F protein. As another example, the mutant of the RSV F protein may be obtained by replacing a C-terminal transmembrane insoluble region of the RSV F protein with a segment of a soluble region of the RSV F protein and at least one of a disulfide bond mutation, a charged amino acid mutation, and deletion of a segment containing a furin cleavage site in comparison to the wild-type RSV F protein.

In some embodiments, the mutant of the RSV F protein may be obtained by replacing a C-terminal transmembrane insoluble region of the RSV F protein with a segment of a soluble region of the RSV F protein. The C-terminal transmembrane insoluble region of the RSV F protein has an amino acid sequence from position 510 to a last position of an amino acid sequence of the RSV F protein, such as SEQ ID NOs. 1-3. The segment of the soluble region of the RSV F protein is a segment having a rigid structure. The segment of the soluble region of the RSV F protein has an amino acid sequence as from positions 155 to 173, from positions 190 to 204, or from positions 255 to 275 of an amino acid sequence of the RSV F protein, such as SEQ ID NOs. 1-3.

In some embodiments, the mutant of the RSV F protein may be obtained by a disulfide bond mutation. The disulfide bond mutation may include one or more of:

(i) mutating lysine or arginine at position 508 of the amino acid sequence of the RSV F protein to cysteine;
(ii) mutating serine at position 509 of the amino acid sequence of the RSV F protein to cysteine;
(iii) mutating alanine or threonine at position 74 of the amino acid sequence of the RSV F protein to cysteine;
(iv) mutating glutamic acid at position 218 of the amino acid sequence of the RSV F protein to cysteine;
(v) mutating glutamine at position 279 of the amino acid sequence of the RSV F protein to cysteine; and
(vi) mutating alanine at position 241 of the amino acid sequence of the RSV F protein to cysteine.

In some embodiments, the mutant of the RSV F protein may be obtained by a charged amino acid mutation. Each of one or more charged amino acids of the amino acid sequence of the RSV F protein may be mutated to a polar amino acid, a hydrophobic amino acid, or an aromatic amino acid to release electrostatic repulsion in the RSV F protein and enhance the stability of an RSV pre-fusion protein. In some embodiments, the charged amino acid mutation may include mutating glutamic acid at position 60 of the amino acid sequence of the RSV F protein to alanine, glycine, serine, threonine, leucine, methionine, or phenylalanine.

In some embodiments, the mutant of the RSV F protein may be obtained by deletion of a segment containing a furin cleavage site. For example, 28 to 46 amino acids from positions 100 to 147 of the amino acid sequence of the RSV F protein may be deleted.

Pharmaceutical Composition

Also provided a pharmaceutical composition comprising the mutant of the RSV-F protein described above, the nucleic acid molecule and/or vector described elsewhere in the present disclosure. Such composition typically further comprises a pharmaceutically acceptable excipient well-known in the art. Such compositions are generally for immunizing subjects against a disease, preferably against RSV. The disease may be any disease associated with (e.g., affected, resulted by) RSV infection. In some embodiments, the pharmaceutical composition of the present disclosure may be considered a vaccine. Pharmaceutical compositions of the present disclosure may comprise the RSV-F protein, nucleic acid (preferably RNA) and/or carrier (preferably lipid nanoparticle) in plain water (e.g. "w.f.i.") or in a buffer e.g. a phosphate buffer, a Tris buffer, a borate buffer, a succinate buffer, a histidine buffer, or a citrate buffer. Pharmaceutical compositions of the present disclosure may include sodium salts (e.g. sodium chloride) to give tonicity. Pharmaceutical compositions of the present disclosure may include metal ion chelators (in particular, in embodiments wherein such compositions comprise RNA). These can prolong RNA stability by removing ions which can accelerate phosphodiester hydrolysis. Thus, such compositions may include one or more of EDTA, EGTA, BAPTA, pentetic acid, etc. A citrate salt, such as sodium citrate, can also act as a chelator, while advantageously also providing buffering activity. Pharmaceutical compositions of the present disclosure may include one or more preservatives, such as thiomersal or 2-phenoxyethanol. Mercury-free compositions are preferred, and preservative-free vaccines can be prepared. Pharmaceutical compositions of the present disclosure may be aseptic or sterile.

Pharmaceutical compositions of the present disclosure may further comprise an adjuvant (i.e. an agent that enhances an immune response in a non-specific manner), in particular, but not exclusively, when comprising an RSV-F protein of the present disclosure. Common adjuvants include suspensions of minerals (e.g. alum, aluminum hydroxide, aluminum phosphate) onto which RSV-F proteins may be adsorbed; emulsions, including water-in-oil, and oil-in-water (and variants thereof, including double emulsions and reversible emulsions), liposaccharides, lipopolysaccharides, immunostimulatory nucleic acids (such as CpG oligonucleotides), liposomes, Toll Receptor agonists (particularly, TLR2, TLR4, TLR7/8 and TLR9 agonists), and various combinations of such components. In some embodiments, the adjuvant is a TLR7 agonist, such as imidazoquinoline or imiquimod. In some embodiments, the adjuvant is an aluminum salt, such as aluminum hydroxide, aluminum phosphate, aluminum sulphate. The adjuvants described herein can be used singularly or in any combination, such as alum/TLR7 (also called AS37). Pharmaceutical compositions of the present disclosure may comprise a saponin as an adjuvant, e.g. saponin fraction QS21 (see, e.g. [30]). QS21 may be used in substantially pure form, e.g. at least 80% pure, such as at least 85, 90%, 95% or at least 98% pure. Pharmaceutical compositions of the present disclosure (preferably when comprising a lipid nanoparticle comprising a nucleic acid of the present disclosure, preferably RNA) may be lyophilised.

Pharmaceutical compositions of the present disclosure may be gluten free. Pharmaceutical compositions of the present disclosure may be prepared as injectables, either as solutions or suspensions. The composition may be prepared for pulmonary administration e.g. by an inhaler, using a fine spray. The composition may be prepared for nasal, aural or ocular administration e.g. as spray or drops. Injectables for intramuscular administration are typical.

Pharmaceutical compositions of the present disclosure comprise an immunologically effective amount of RSV-F protein. nucleic acid (preferably RNA) and/or carrier (preferably lipid nanoparticle), as well as any other components, as needed. By "immunologically effective amount", it is meant that the administration of that amount to an individual, either in a single dose or as part of a series, is effective for treatment or prevention, preferably prevention of RSV. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other rel-evant factors. It is expected that the amount will fall in a relatively broad range that can be determined through routine trials.

Methods of Treatment

Also provided is a method for raising an immune response in a subject and/or a method for the prevention, reduction or treatment of a disease associated with RSV infection in a subject. These methods include the step of administering an effective amount of the mutant of the RSV F protein, the nucleic acid molecule, the vector or pharmaceutical composition (e.g., vaccine) of the present disclosure to the subject (preferably a subject in need of such administration). In some embodiments, the subject is a vertebrate, preferably a mammal, more preferably a human or large veterinary mammal (e.g., horses, cattle, deer, goats, pigs), even more preferably a human. The administration may be given by routes e.g. a parenteral prime and mucosal boost, a mucosal prime and parenteral boost, etc. The mutant of the RSV F protein, the nucleic acid molecule, the vector or pharmaceutical compositions of the present disclosure may generally be administered directly to the subject. Direct delivery may be accomplished by parenteral injection (e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Preferably, the mutant of the RSV F protein, the nucleic acid molecule, the vector or pharmaceutical composition of the present disclosure may be administered intramuscularly or intradermally (in particular via a needle such as a hypodermic needle), more preferably intramuscularly. The mutant of the RSV F protein, the nucleic acid molecule, the vector or pharmaceutical composition of the present disclosure may be used to elicit systemic and/or mucosal immunity. The subject of a method of vaccination according to the present disclosure may be a child (preferably an infant) or adult (preferably an older adult or pregnant female).

Also provided is a method for detecting RSV infection in a subject. The method includes determining whether a sample of the subject is suffered from the RSV infection by detecting a titer of a binding antibody in the sample (e.g., blood, serum) using the mutant of the RSV F protein or produced by the nucleic acid molecule, or the cell as a coating reagent.

EXAMPLES

The present disclosure is further described below in connection with the following examples.

Example 1: Design and Expression of Mutants of an RSV F Protein

In total, more than 400 mutants of the RSV F protein have been evaluated in the present disclosure. This example summarizes the design and expression of positive control molecules (SC-TM, DS-CavI, 847) and seven representative mutants of the RSV F protein (each of which is labeled by a unique identifier, such as YK001Ag222, YK001Ag399, etc.). The design and expression of exemplary mutants of the RSV F protein are provided in Table 1. Each of the seven exemplary mutants was designed and prepared based on the amino acid sequences described in SEQ ID NOs. 1-3. Methods for expressing and purifying these exemplary mutants of the RSV F protein are described in Examples 2 and 4, and methods for determining the expression of these exemplary mutants of the RSV F protein (also referred to as RSV F protein mutants) are described in Example 3. The expression of the mutants of the RSV F protein is the amount of a target protein in the supernatant of the cells described in Example 2 of the present disclosure.

The antibody D25 specifically recognizes the F protein in the RSV pre-fusion conformation, whereas the antibody AM14 specifically recognizes only the trimerized pre-fusion F protein. To ensure that the improved mutant of the RSV F protein is in the pre-fusion conformation and a trimerized state, the binding of the mutant to antibodies D25 and AM14 was measured in this example. As shown in Table 1 and FIG. 2, all seven representative molecules can specifically bind to two antibodies, and the difference in expression respectively measured by the two antibodies was not significant (less than double). It is indicated that the conformations of the seven representative molecules and the positive control molecules were similar, and all of them can present the pre-fusion trimerization conformation. The representative molecules, YK001Ag399, YK001Ag401, YK001Ag404, YK001Ag410, and YK001Ag411 do not contain heterologous trimerization domains and have successfully achieved the replacement of the heterologous folden with their own homodimerized S155-S173 amino acids without affecting the trimerization of the target protein. The YK001Ag406 and YK001Ag407 do not contain heterologous trimerization domains and have successfully achieved the replacement of the heterologous folden with their own homodimerized S190-L204 and S255-S275 amino acids without affecting the trimerization of the target protein.

{21 TABLE 1

Sequence design and expression of exemplary RSV F protein mutants

| Mutant ID | Furin deletion | Site mutation | C-terminal trimerization mutation | Expression of pre-fusion F protein (mg/L) (measured by binding to antibody D25) | Expression of trimeric pre-fusion F protein (mg/L) (measured by binding to antibody AM14) |
|---|---|---|---|---|---|
| SC-TM (positive control) | Sequence found in Krarup, A., et al. (2015). *A highly stable prefusion RSV F vaccine derived from structural analysis of the fusion mechanism.* Nat Commun 6: 8143" | | | 86.31 | 144.8 |
| DS-CavI (positive control) | Sequence found in McLellan, J. S., et al. (2013). *Structure-based design of a fusion glycoprotein vaccine for respiratory syncytial virus.* Science 342(6158): 592-598 | | | 51.24 | 56.4 |
| pXCS847 (positive control) | Sequence found in the pXCS847 molecule in patent application CN108738312A | | | 32.89 | 35.7 |
| YK001Ag222 | Deletion of 37 amino acids between positions 105 and 143 | / | foldon | 84.08 | 89.2 |
| YK001Ag400 | | E60L | foldon | 156.28 | 132.4 |
| YK001Ag402 | | E60L, E218C, A74C | foldon | 37.69 | 39.7 |
| YK001Ag403 | | E60L, Q279C, A241C | foldon | 21.52 | 31.2 |
| YK001Ag401 (RSV A) | | E60L, K508C, S509C | Replacement of D510 and subsequent amino acids with S155-S173 | 199.32 | 161.4 |
| YK001Ag404 (RSV A) | | E60L, E218C, A74C, K508C-S509C | | 32.69 | 31.5 |
| YK001Ag399 (RSV A) | | E60L, Q279C-A241C, K508C-S509C | | 10.65 | 11.6 |
| YK001Ag406 (RSV A) | | | Replacement of D510 and subsequent amino acids with S190-L204 | 5.6 | 6.8 |
| YK001Ag407 (RSV A) | | | Replacement of D510 and subsequent amino acids with S255-S275 | 5.3 | 6.9 |
| YK001Ag410 (AHV80758, RSV B) | The same as YK001Ag399 | | | 5.1 | 7.1 |
| YK001Ag411 (AVQ93588.1, RSV B) | The same as YK001Ag399 | | | 6.9 | 9.3 |

Example 2: Construction of an Expression Vector and Small-Scale Expression of Mutants of an RSV F Protein The coding nucleic acid sequence of each of the RSV F protein mutants was codon optimized and synthesized using Chinese hamster ovary (CHO) cells as the host, cloned into the YKVGS001 vector using HindIII and NotI restriction sites, and plasmid was extracted for further transfection.

Large-volume transfections were performed using fast-growing Expi 293 cells with good cytomorphic status as the transfection host, and the viable cell density of the seeding cells was adjusted to 3 million cells per milliliter before transfection, and 20 mL of a cell solution was used for each sample for transfection. Each sample was performed using 20 μg of plasmid and 100 μg of PEI MAX® transfection reagent, which was diluted with 600 μL of OPM-293CD05 medium, respectively, and gently added dropwise to the diluted plasmid and incubated at room temperature for 8 minutes to prepare the plasmid complex. At the incubation, the prepared plasmid complex was slowly dripped into the cell solution to be transfected, and the cell solution was placed in a shaker at 37° C., 8% $CO_2$ at 200 rpm. After transfection for 18-24 hours, 10% culture volume of BalanCD CHO Feed 4 (0.8×) (V/V) was added to each vial of transfected cells respectively and the cell status was monitored daily. The transfection cycle was usually 4 days, and the supernatant of the cell culture fluid was harvested on day 4 for the determination of the expression and transferred for purification.

Example 3: Expression and Stability Assay (Using Monoclonal Antibodies D25 and AM14) of Mutants of the RSV F Protein The cell supernatant obtained in Example 2 of the present disclosure was filtered by a disposable 0.22 μm sterile filter and dispensed. The dispensed samples were directly assayed for the determination of expression of the target protein of the supernatant or placed in a thermostat at 60° C. for 1 h to examine the stability of samples under a high-temperature condition. The Gator™ molecular interaction detector based on the principle of biofilm photointerference was used to calculate the cell expression in the supernatant and the stability of the samples for the target protein by testing the binding rate of monoclonal antibody D25 or AM14 to the RSV F mutants through the specificity of the RSV fusion precursor.

Specific test process: protein A probe to captures monoclonal antibody D25 or AM14 after being equilibrated for 50 s, performs binding reaction with the supernatants of RSV F protein mutants for 200 Safter being equilibrated for 120 s, followed by a 120 s dissociation reaction to test the binding interaction of the designed RSV F protein mutants to the monoclonal antibody D25 or AM14. The amount of the target protein was calculated based on standard curves established with standards of known concentration.

Figure 3:
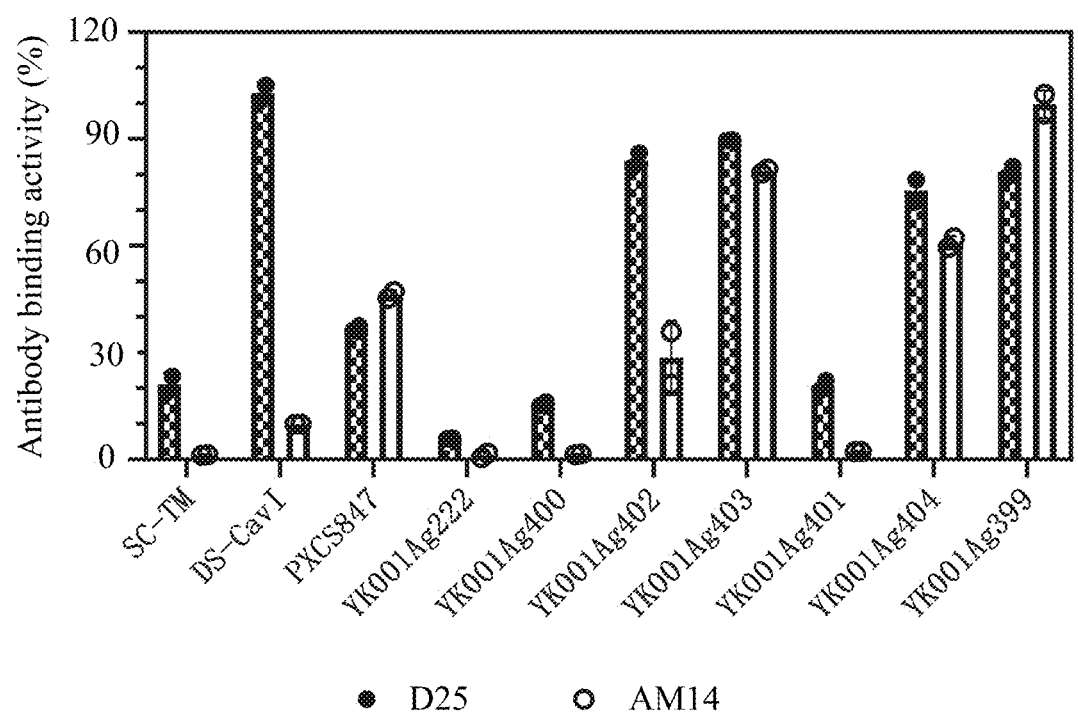
FIG. 3 is a graph illustrating measured F-protein stability using pre-fusion F protein specific antibodies D25 and AM14, with SC-TM, DS-CavI, and pXCS847 as positive controls.

In some embodiments, the results of measured expression of selected RSV F protein mutants are shown in Table 1 and FIG. 2 (part mutants), and the results of stability detection are shown in Table 2 and FIG. 3 (part mutants). After the improved mutation design in the present disclosure, most of the RSV F protein mutants were able to stably present the prefusion conformation. After being placed at 60° C. for 1 hour, the RSV F protein mutants, such as YK001Ag403, YK001Ag404, YK001Ag399, YK001Ag406, YK001Ag407, YK001Ag410, and YK001Ag411, were still able to maintain a high binding activity with monoclonal antibodies D25 and AM14.

TABLE 2

Stability results of the exemplary RSV F protein mutants

| Mutant ID | Stability (measured by binding to antibodies D25 and AM14) | |
|---|---|---|
| | Activity of antibody D25 after 1 h at 60° C. (%) | Activity of antibody AM14 after 1 h at 60° C. (%) |
| SC-TM (positive control) | 21.0 | 1.3 |
| DS-CavI (positive control) | 102.9 | 9.9 |
| pXCS 847 (positive control) | 36.8 | 46.1 |
| YK001Ag222 | 5.8 | 1.1 |
| YK001Ag400 | 15.6 | 1.4 |
| YK001Ag402 | 84.0 | 28.6 |
| YK001Ag403 | 89.7 | 81.0 |
| YK001Ag401 | 20.8 | 2.2 |
| YK001Ag404 | 75.4 | 60.9 |
| YK001Ag399 | 80.8 | 99.8 |
| YK001Ag406 | 60.4 | 45.47 |
| YK001Ag407 | 77.22 | 52.65 |
| YK001Ag410 | 88.68 | 67.66 |
| YK001Ag411 | 91.37 | 69.54 |

Comparing the stability data of YK001Ag400 with YK001Ag401, YK001Ag402 with YK001Ag404, and YK001Ag403 with YK001Ag399, when all the mutation designs are the same except for the C-terminal mutation (the K508C-S509C mutation is immediately adjacent to the C-terminal, and is categorized to the C-terminal mutation to increase the C-terminal trimeric interaction), trimerization and stability of the target protein are not affected by replacing the heterologous foldon with its own homologous S155-S173 peptide.

Comparing the stability data of YK001Ag400 with YK001Ag402, and YK001Ag401 with YK001Ag404, when the rest of the mutation designs are the same, the introduction of the A74C-E218C mutations can substantially increase the stability of the pre-fusion trimer of the target protein.

Comparing the stability data of YK001Ag401 with YK001Ag399, and YK001Ag400 with YK001Ag403, when the rest of the mutation designs are the same, the introduction of the Q279C-A241C mutations can also greatly increase the stability of the pre-fusion trimer of the target protein.

Comparing the expression and stability data of YK001Ag222 and YK001Ag400, when the rest of the mutation designs are all the same, the introduction of the E60L mutation can enhance the protein expression and stability to a certain extent.

Comparing the expression and stability data of YK001Ag410 and YK001Ag411 with YK001Ag399, the mutations with respect to different wild type RSV F proteins can achieve similar effects, showing that the mutations can applied to all the wild type RSV F proteins.

Comparing the expression and stability data of YK001Ag406 and YK001Ag407 with YK001Ag399, when the rest of the mutations are the same, the introduction of different segments of the soluble region of the RSV F protein mutations can achieve similar effects.

Example 4: Purification of the RSV F Protein Mutants

First, the pH of the clarified harvest liquid was adjusted to 7.0 using 0.5 M sodium hydroxide solution and the conductivity of the clarified harvest liquid was adjusted to no more than 8.0 mS/cm using 20 mM phosphate buffer with pH 7.0.

Second, the pretreated sample was uploaded onto a strong cation exchange chromatography column pre-equilibrated with 20 mM phosphate buffer with pH 7.0, and after uploading, a gradient elution using 20 mM phosphate buffer with pH 7.0 and 1 M NaCl buffer was carried out, and the eluate containing the target protein fraction was collected.

Third, the pH of the strong cation exchange chromatography eluate was adjusted to 7.5 using 0.5 M sodium hydroxide solution.

Fourth, after sample treatment, the samples were uploaded onto a composite mode chromatography column pre-equilibrated with 20 mM phosphate buffer with pH 7.5, and after uploading, a gradient elution using 20 mM phosphate buffer with pH 7.5 and 1 M NaCl buffer was carried out, and the eluate containing the target protein fraction was collected.

Fifth, the complex mode chromatography eluate was uploaded to a volume exclusion chromatography column pre-equilibrated using 1×PBS with pH 7.4, and the eluate containing the target protein fractions was collected, i.e., a high-purity protein sample was obtained.

Figure 4:
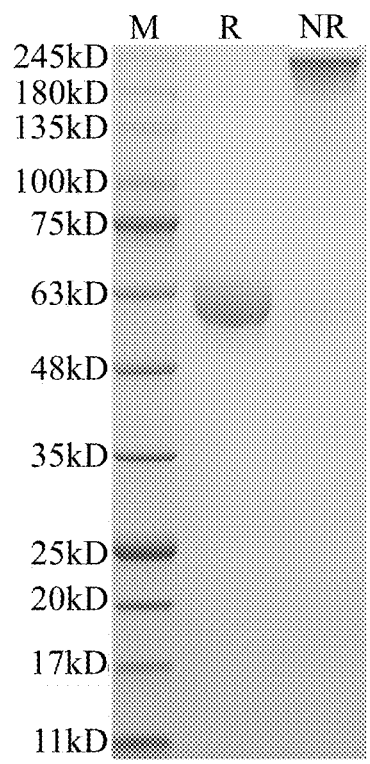
FIG. 4 is a schematic diagram illustrating a sodium dodecyl sulfate-polyacrylamide gel electrophoresis (SDS-PAGE) analysis of a purified protein of a mutant YK001Ag399 of a F protein under reduced (R) and non-reduced (NR) conditions.

The purification results of the selected representative RSV F mutant YK001Ag399 are shown in FIG. 4. After purification, the target protein can be obtained with high electrophoretic purity and the trimeric conformation of F protein may be maintained. In the present disclosure, taking the representative RSV F mutant YK001Ag399 as an example, the deletion of the furin cleavage site introduced therein is to maintain the pre-fusion conformation of the F protein, and the introduction of other mutations is to enhance the stability of the protein. The C-terminal mutation design is to use a segment of the soluble region of the F protein to replace the transmembrane insoluble region of the C-terminal of the F protein, which can play a role in maintaining the trimeric conformation of the F protein.

Example 5: Distribution Analysis of Particle Sizes of a Selected Pre-Fusion RSV F Protein Mutant To analyze the size distribution of the designed RSV F protein mutant, the purified sample was analyzed by the SEC-HPLC method. Specifically, the column was Agilent Bio SEC-3 (3 μm, 150 Å, 4.6*300 mm), the detection wavelength was 280 nm, the mobile phase was 1×PBS, the flow rate was 0.4 ml/min, the injection volume was 10 μl, and the isocratic elution was 15 min. The test solution was prepared as follows: 50 μl of the sample was taken in a 1.5 ml centrifuge tube, and after centrifugation at 10,000 rpm for 1 min, the supernatant was taken in the liquid-phase vial containing an insert tube, and then set aside. The protein was eluted and separated according to the molecular size of the component to be tested.

Figure 5:
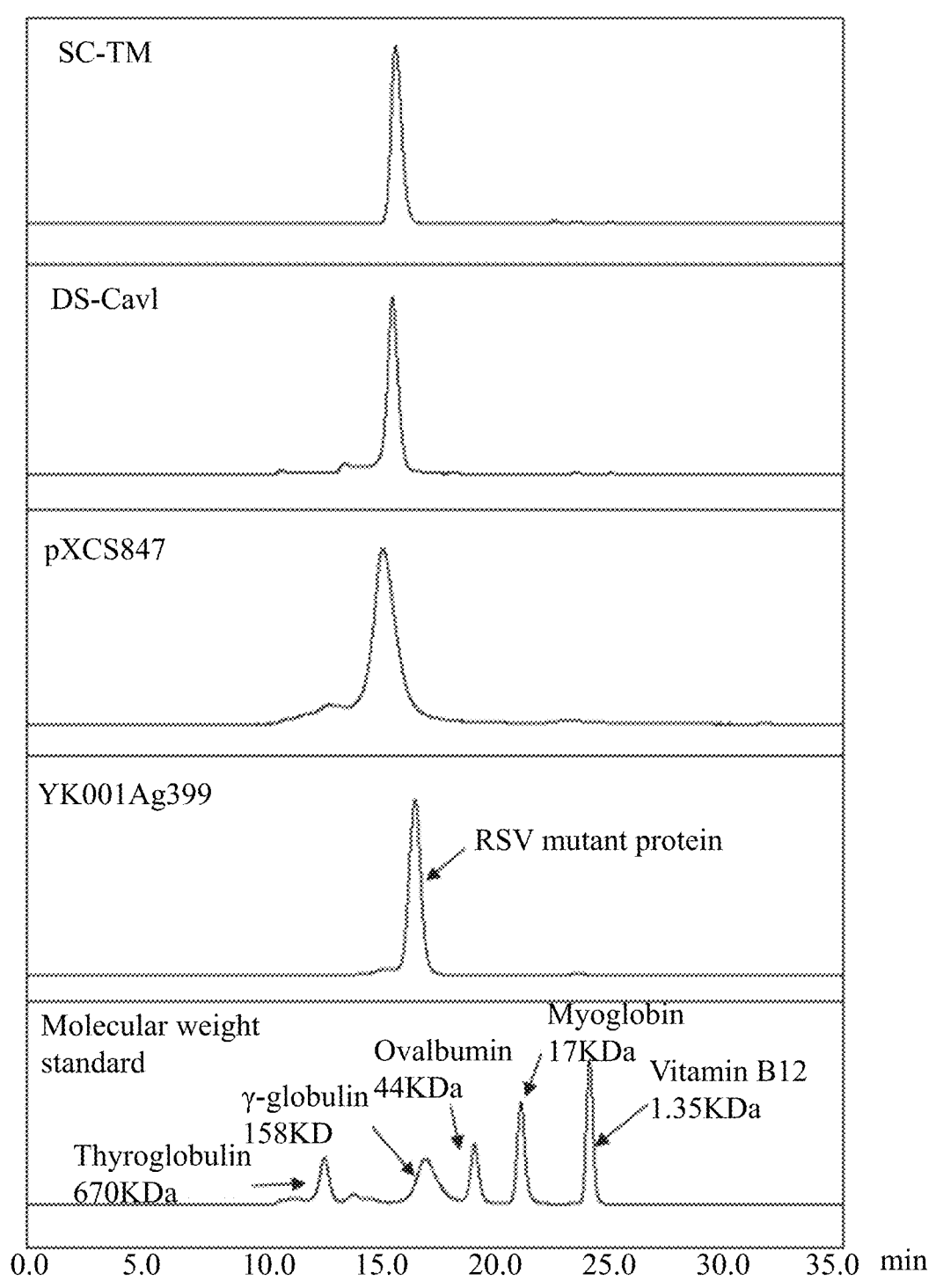

The molecular weight of the RSV F protein mutant monomer described in the present disclosure is about 53 KDa. As shown in FIG. 5, the retention time of the peak of the selected RSV F protein mutant is close to that of the γ-globin with a molecular weight of 158 KDa, which confirms that the RSV F mutant is in trimeric conformation.

Example 6: Structural Thermal Stability of the Selected Pre-Fusion RSV F Protein Mutant To examine the thermal stability of the RSV F protein mutant, this example was performed to assess the particle size and thermal denaturation of the antigen by the Prometheus Panta method. Specifically, 50 μl of the test material was taken, centrifuged at 15000 g for 10 min at 8° C. and loaded into a capillary tube (Manufacturer: Nano Temper, Item No.: PR-C002), and loaded into a tray, 3 replicate wells for each test material. The Thermal Unfolding module in the software of the equipment was selected, detection was performed with a start temperature of 25° C., an end temperature of 95° C., and a warming rate 1° C./min.

The results of the structural thermal stability examination of the representative RSV F protein mutant were shown in Table 3, and the melting temperature (Tm) value of the YK001Ag399 was significantly higher than those of SC-TM and DS-CavI positive controls and also similar to those of the pXCS847 positive control, proving that the improved designed protein mutant has excellent structural thermal stability.

TABLE 3

Structural thermal stability data of exemplary RSV protein mutants

| Mutant ID | Tm1/° C. ø* | Tm1/° C. σ* | Tm2/° C. ø* | Tm2/° C. σ* |
|---|---|---|---|---|
| SC-TM (positive control) | 61.64 | 0.12 | 81.88 | 0.32 |
| DS-CavI (positive control) | NA | NA | 85.07 | 0.01 |
| pXCS 847 (positive control) | 68.02 | 0.01 | 86.06 | 0.07 |
| YK001Ag399 | 68.12 | 0.09 | 86.79 | 0.18 |

ø* denotes the mean, σ* denotes the variance, and NA denotes that abnormal data that cannot be fitted.

Figure 6:
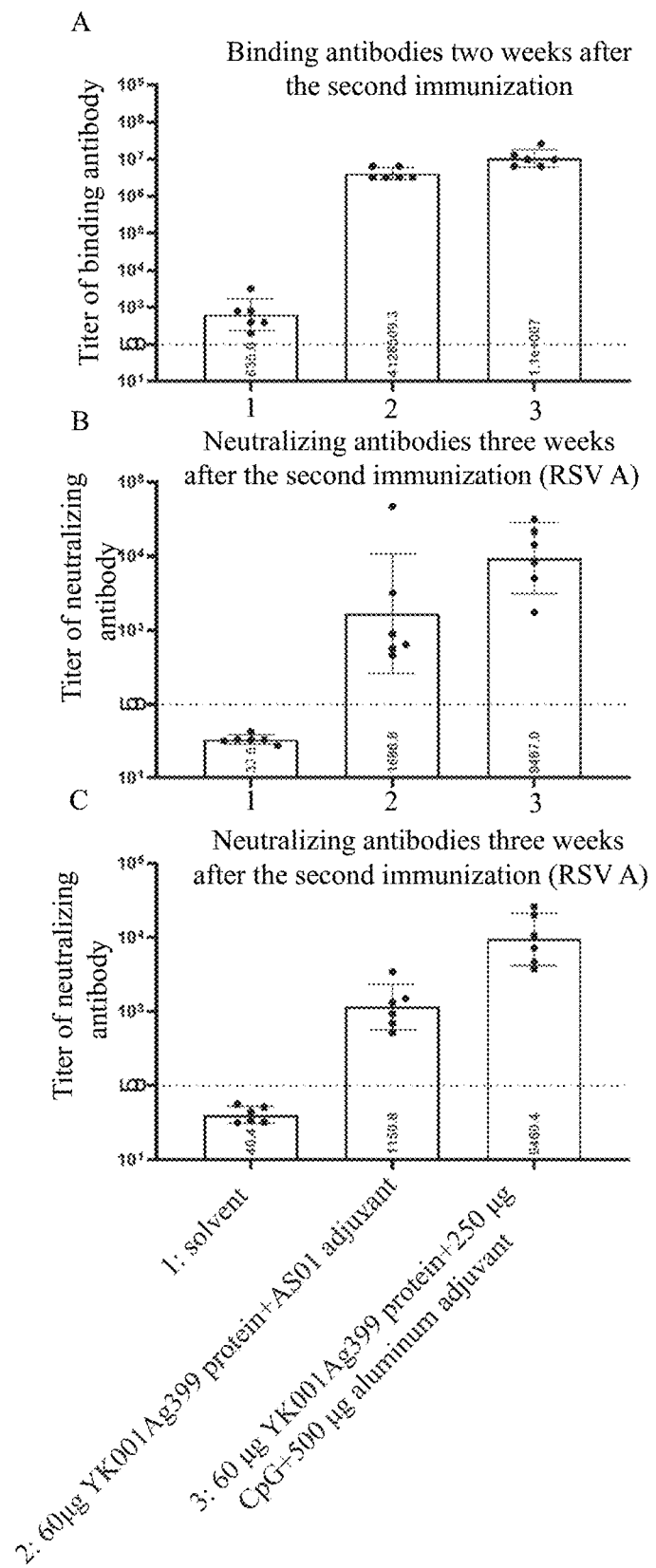
FIG. 6 is a schematic diagram illustrating assessment results of immunogenicity (binding antibody) of vaccine formulations prepared with the mutant YK001Ag399 as a core component.

Example 7: Immunologic Response of the Improved Designed RSV F Protein Mutant in Mice To study the immunogenicity of the RSV F protein mutant provided by the present disclosure, the inventors of the present disclosure made vaccine compositions (0.5 ml/dose) containing different adjuvants with a representative design molecule, YK001Ag399, as the antigen, which was specified in Table 4. Immunogenicity of the vaccine compositions was examined in SPF-grade female 6-8-week-old BALB/c mice in groups of 6 mice each, totaling 3 groups. Immunization was performed by intramuscular injection in a volume of 50 μl/dose/each mouse (1/10 human proposed dose). Each mouse was immunized a total of 2 times at 3-week intervals. Blood was collected from each group of mice two weeks after the second immunization, and IgG antibody titers against the F protein in serum were detected by ELISA (FIG. 6-A). Blood was collected from each group of mice three weeks after the second immunization, and the titer of the serum neutralizing antibody were detected by a neutralization assay based on the wild-type A-type and B-type live viruses (FIGS. 6B and 6C).

TABLE 4

Formulation of different RSV vaccine compositions

| Groups | Dose/0.5 ml |
|---|---|
| 1 | Solvent |
| 2 | 60 μg YK001Ag399 protein, AS01 adjuvant |

TABLE 4-continued

Formulation of different RSV vaccine compositions

| Groups | Dose/0.5 ml |
| --- | --- |
| 3 | 60 μg YK001Ag399 protein, 250 μg CpG, 500 μg aluminum adjuvant |

Compared with the solvent control group (group 1), high levels of binding antibodies against the F protein can be detected in the sera of mice from all experimental groups two weeks after the second immunization, and the sera of mice from all experimental groups three weeks after the second immunization were able to efficiently neutralize the replication of the wild-type type-A and type-B live viruses in vitro cells, suggesting that the RSV F protein mutant provided by the present disclosure have excellent immunogenicity and that they can induce cross-protection against both A and B viruses when used as a vaccine product.

The above is only a preferred embodiment of the present disclosure and is not intended to limit the present disclosure. It should be pointed out that, for the person of ordinary skill in the art, a number of improvements and variations can be made without departing from the technical principles of the present disclosure, and these improvements and variations are within the scope of protection of the present disclosure.

```
                            SEQUENCE LISTING

Sequence total quantity: 4
SEQ ID NO: 1              moltype = AA  length = 574
FEATURE                   Location/Qualifiers
source                    1..574
                          mol_type = protein
                          organism = synthetic construct
SEQUENCE: 1
MELPILKTNA ITTILAAVTL CFASSQNITE EFYQSTCSAV SKGYLSALRT GWYTSVITIE    60
LSNIKENKCN GTDAKVKLIK QELDKYKNAV TELQLLMQST PAANSRARRE LPRFMNYTLN   120
NTKNTNVTLS KKRKRRFLGF LLGVGSAIAS GIAVSKVLHL EGEVNKIKSA LLSTNKAVVS   180
LSNGVSVLTS KVLDLKNYID KQLLPIVNKQ SCSISNIETV IEFQQKNNRL LEITREFSVN   240
AGVTTPVSTY MLTNSELLSL INDMPITNDQ KKLMSSNVQI VRQQSYSIMS IIKEEVLAYV   300
VQLPLYGVID TPCWKLHTSP LCTTNTKEGS NICLTRTDRG WYCDNAGSVS FFPQAETCKV   360
QSNRVFCDTM NSLTLPSEVN LCNIDIFNPK YDCKIMTSKT DVSSSVITSL GAIVSCYGKT   420
KCTASNKNRG IIKTFSNGCD YVSNKGVDTV SVGNTLYYVN KQEGKSLYVK GEPIINFYDP   480
LVFPSDEFDA SISQVNEKIN QSLAFIRKSD ELLHNVNAGK STTNIMITTI IIVIIVILLA   540
LIAVGLLLYC KARSTPVTLS KDQLSGINNI AFSN                              574

SEQ ID NO: 2              moltype = AA  length = 574
FEATURE                   Location/Qualifiers
source                    1..574
                          mol_type = protein
                          organism = synthetic construct
SEQUENCE: 2
MELLIHRSSA IFLTLAINAL YLTSSQNITE EFYQSTCSAV SRGYFSALRT GWYTSVITIE    60
LSNIKETKCN GTDTKVKLIK QELDKYKNAV TELQLLMQNT PAANNRARRE APQYMNYTIN   120
TTKNLNVSIS KKRKRRFLGF LLGVGSAIAS GIAVSKVLHL EGEVNKIKNA LLSTNKAVVS   180
LSNGVSVLTS KVLDLKNYIN NQLLPIVNQQ SCRISNIETV IEFQQKNSRL LEITREFSVN   240
AGVTTPLSTY MLTNSELLSL INDMPITNDQ KKLMSSNVQI VRQQSYSIMS IIKEEVLAYV   300
VQLPIYGVID TPCWKLHTSP LCTTNIKEGS NICLTRTDRG WYCDNAGSVS FFPQADTCKV   360
QSNRVFCDTM NSLTLPSEVS LCNTDIFNSK YDCKIMTSKT DISSSVITSL GAIVSCYGKT   420
KCTASNKNRG IIKTFSNGCD YVSNKGVDTV SVGNTLYYVN KLEGKNLYVK GEPIINYYDP   480
LVFPSDEFDA SISQVNEKIN QSLAFIRRSD ELLHNVNTGK STTNIMITAI IIVIIVVLLS   540
LIAIGLLLYC KAKNTPVTLS KDQLSGINNI AFSK                              574

SEQ ID NO: 3              moltype = AA  length = 574
FEATURE                   Location/Qualifiers
source                    1..574
                          mol_type = protein
                          organism = synthetic construct
SEQUENCE: 3
MELLIHRSSA IFLTLAINAL YLTSSQNITE EFYQSTCSAV SRGYLSALRT GWYTSVITIE    60
LSNIKETKCN GTDTKVKLIK QELDKYKNAV TELQLLMQNT PAVNNRARRE APQYMNYTIN   120
TTKNLNVSIS KKRKRRFLGF LLGVGSAIAS GIAVSKVLHL EGEVNKIKNA LQLTNKAVVS   180
LSNGVSVLTS KVLDLKNYIN NQLLPIVNQQ SCRISNIETV IEFQQKNSRL LEITREFSVN   240
AGVTTPLSTY MLTNSELLSL INDMPITNDQ KKLMSSNVQI VRQQSYSIMS IIKEEVLAYV   300
VQLPIYGVID TPCWKLHTSP LCTTNIKEGS NICLTRTDRG WYCDNAGSVS FFPQADTCKV   360
QSNRVFCDTM NSLTLPSEVS LCNTDIFNSK YDCKIMTSKT DISSSVITSL GAIVSCYGKT   420
KCTASNKNRG IIKTFSNGCD YVSNKGVDTV SVGNTLYYVN KLEGKNLYVK GEPIINYYDP   480
LVFPSDEFDA SISQVNEKIN QSLAFIRRSD ELLHNVNTGK STTNIMITAI IIVIIVVLLS   540
LIAVGLLLYC KAKNTPVTLS KDQLSGINNI AFSK                              574

SEQ ID NO: 4              moltype = AA  length = 484
FEATURE                   Location/Qualifiers
source                    1..484
                          mol_type = protein
                          organism = synthetic construct
SEQUENCE: 4
MKWVTFLLLL FISGSAFSQN ITEEFYQSTC SAVSKGYLSA LRTGWYTSVI TIELSNIKEN    60
KCNGTDAKVK LIKQELDKYK NAVTELQLLM QSTPAANSGV GSAIASGIAV SKVLHLEGEV   120
NKIKSALLST NKAVVSLSNG VSVLTSKVLD LKNYIDKQLL PIVNKQSCSI SNIETVIEFQ   180
```

-continued

```
QKNNRLLEIT REFSVNAGVT TPVSTYMLTN SELLSLINDM PITNDQKKLM SSNVQIVRQQ    240
SYSIMSIIKE EVLAYVVQLP LYGVIDTPCW KLHTSPLCTT NTKEGSNICL TRTDRGWYCD    300
NAGSVSFFPQ AETCKVQSNR VFCDTMNSLT LPSEVNLCNI DIFNPKYDCK IMTSKTDVSS    360
SVITSLGAIV SCYGKTKCTA SNKNRGIIKT FSNGCDYVSN KGVDTVSVGN TLYYVNKQEG    420
KSLYVKGEPI INFYDPLVFP SDEFDASISQ VNEKINQSLA FIRKSSKVLH LEGEVNKIKS    480
ALLS                                                                484
```

What is claimed is:

1. A mutant of a respiratory syncytial virus (RSV) fusion (F) protein, which is obtained by replacing a C-terminal transmembrane insoluble region of the RSV F protein with a segment of a soluble region of the RSV F protein, and deleting the segment containing a furin cleavage site of the amino acid sequence of the RSV F protein, wherein the segment containing the furin cleavage site includes 28 to 46 amino acids from positions 100 to 147 of SEQ ID NO.1, wherein the segment of the soluble region of the RSV F protein is the segment having a rigid structure;

the RSV F protein has the amino acid sequence of SEQ ID NO. 1, and the segment of the soluble region of the RSV F protein has an amino acid sequence as from positions 155 to 173, from positions 190 to 204, or from positions 255 to 275 of SEQ ID NO. 1;

the C-terminal transmembrane insoluble region of the RSV F protein has an amino acid sequence from position 510 to the last position of SEQ ID NO. 1, the last position of SEQ ID NO. 1 being asparagine at position 574; and lysine at position 508 and serine at position 509 of SEQ ID NO. 1 are respectively mutated to cysteine.

2. The mutant of claim 1, further comprising at least one disulfide bond mutation that adds at least one disulfide bond to SEQ ID NO. 1 to enhance stability of the RSV F protein.

3. The mutant of claim 2, wherein the at least one disulfide bond mutation comprises:

mutating alanine at position 74 and glutamic acid at position 218 of SEQ ID NO. 1 to cysteine; and mutating glutamine at position 279 and alanine at position 241 of SEQ ID NO. 1 to cysteine.

4. The mutant of claim 1, wherein each of one or more charged amino acids of the amino acid sequence of the RSV F protein is mutated to a polar amino acid, a hydrophobic amino acid, or an aromatic amino acid to release electrostatic repulsion in the RSV F protein and enhance the stability of an RSV pre-fusion protein; and the one or more charged amino acids include glutamic acid at position 60 of SEQ ID NO. 1, which is mutated to alanine, glycine, serine, threonine, leucine, methionine, or phenylalanine.

5. A nucleic acid molecule encoding the mutant of the RSV F protein of claim 1.

6. A vector, comprising the nucleic acid molecule of claim 5.

7. A cell, wherein the cell expresses the mutant of the RSV F protein of claim 1.

8. A vaccine, comprising the mutant of the RSV F protein of claim 1.

9. A pharmaceutical composition, comprising the mutant of the RSV F protein of claim 1.

10. The mutant of claim 1, wherein the segment containing the furin cleavage site includes 37 amino acids between positions 105 and 143 of SEQ ID NO. 1.

* * * * *